US012685525B2

(12) United States Patent
Wilson et al.

(10) Patent No.: US 12,685,525 B2
(45) Date of Patent: Jul. 21, 2026

(54) EXTERNALLY MAGNETICALLY OPERATED SUTURE ANCHOR

(71) Applicant: Texas Scottish Rite Hospital for Children, Dallas, TX (US)

(72) Inventors: Philip L. Wilson, Pilot Point, TX (US); Henry Ellis, Frisco, TX (US); Brad Anthony Niese, Southlake, TX (US)

(73) Assignee: Texas Scottish Rite Hospital for Children, Dallas, TX (US)

( * ) Notice: Subject to any disclaimer, the term of this patent is extended or adjusted under 35 U.S.C. 154(b) by 0 days.

(21) Appl. No.: 19/174,635

(22) Filed: Apr. 9, 2025

(65) Prior Publication Data

US 2025/0318823 A1     Oct. 16, 2025

Related U.S. Application Data

(60) Provisional application No. 63/632,886, filed on Apr. 11, 2024.

(51) Int. Cl.
    *A61B 17/04*     (2006.01)
    *A61B 17/00*     (2006.01)
(52) U.S. Cl.
    CPC . *A61B 17/0401* (2013.01); *A61B 2017/00411* (2013.01); *A61B 2017/0409* (2013.01); *A61B 2017/0427* (2013.01)
(58) Field of Classification Search
    CPC .................... A61B 17/0401–17/06195; A61B 2017/00411; A61B 2017/0409; A61B 2017/0427; A61B 2017/00876; A61B 2017/0414; A61F 2/0811; A61F 2002/0817–2002/0841
    See application file for complete search history.

(56) References Cited

U.S. PATENT DOCUMENTS

| | | | |
|---|---|---|---|
| 2005/0090827 A1* | 4/2005 | Gedebou | A61F 2/0811 |
| | | | 606/328 |
| 2015/0038976 A1* | 2/2015 | Roschak | A61B 17/0401 |
| | | | 606/104 |
| 2022/0183843 A1 | 6/2022 | Sirhan et al. | |
| 2023/0404568 A1 | 12/2023 | Arai et al. | |

FOREIGN PATENT DOCUMENTS

| | | |
|---|---|---|
| KR | 1020230144584 | 10/2023 |
| WO | 2011128392 A1 | 10/2011 |
| WO | 2022172149 A1 | 8/2022 |

OTHER PUBLICATIONS

Ramirez-Ramirez, M.A., et al., "Simplified magnetic anchor-guided endoscopic submucosal dissectoin: an ex vivo porcine model," Revista de Gastrenterologia de Mexico vol. 87, Sep. 2020, pp. 13-19.
International Search Report and Written Opinion of PCT/US2025/023923 issued by the Korean Intellectual Property Office on Jul. 21, 2025, 12 pp.

* cited by examiner

*Primary Examiner* — Kathleen S Holwerda
*Assistant Examiner* — James R McGinnity
(74) *Attorney, Agent, or Firm* — Edwin S. Flores; Daniel J. Chalker; Chalker Flores, LLP

(57)          ABSTRACT

Provided herein are compositions and methods including a magnetically actuated suture anchor including an anchor magnet configured to be magnetically moved using an external magnet from a first position to a second position, wherein in the first position, a tension is maintained in a suture connected to the magnetically actuated suture anchor and in the second position the tension in the suture is released.

8 Claims, 12 Drawing Sheets

PRIOR ART        PRIOR ART        PRIOR ART

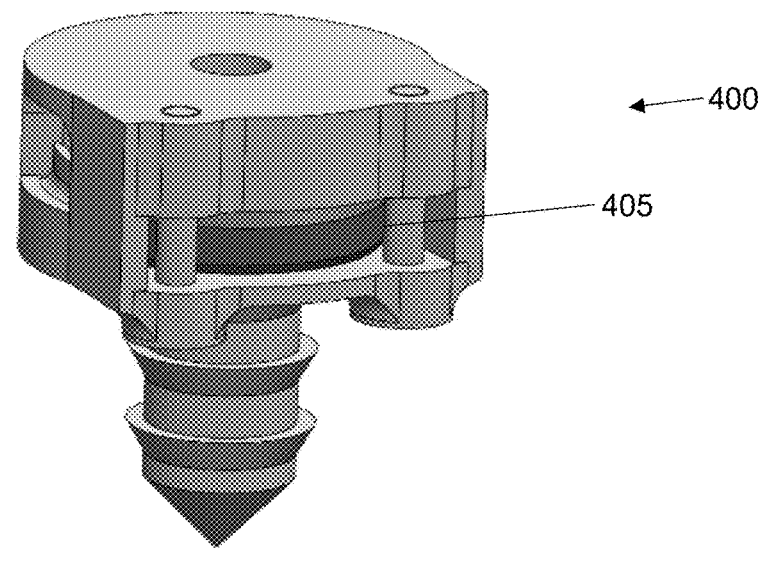
FIG. 4A
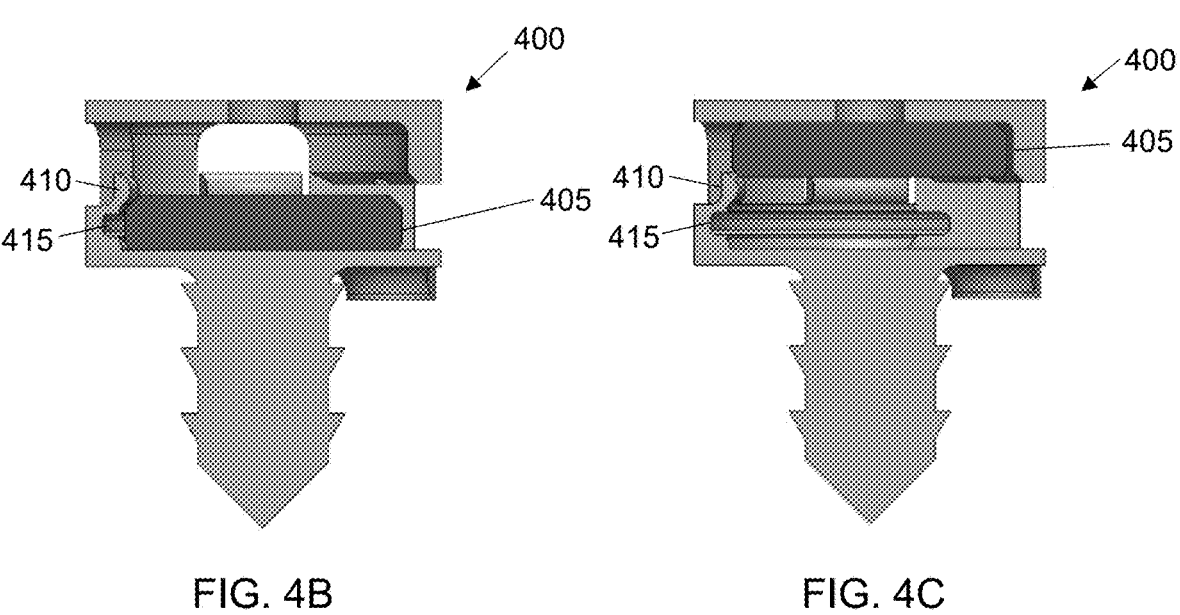
FIG. 4B                    FIG. 4C

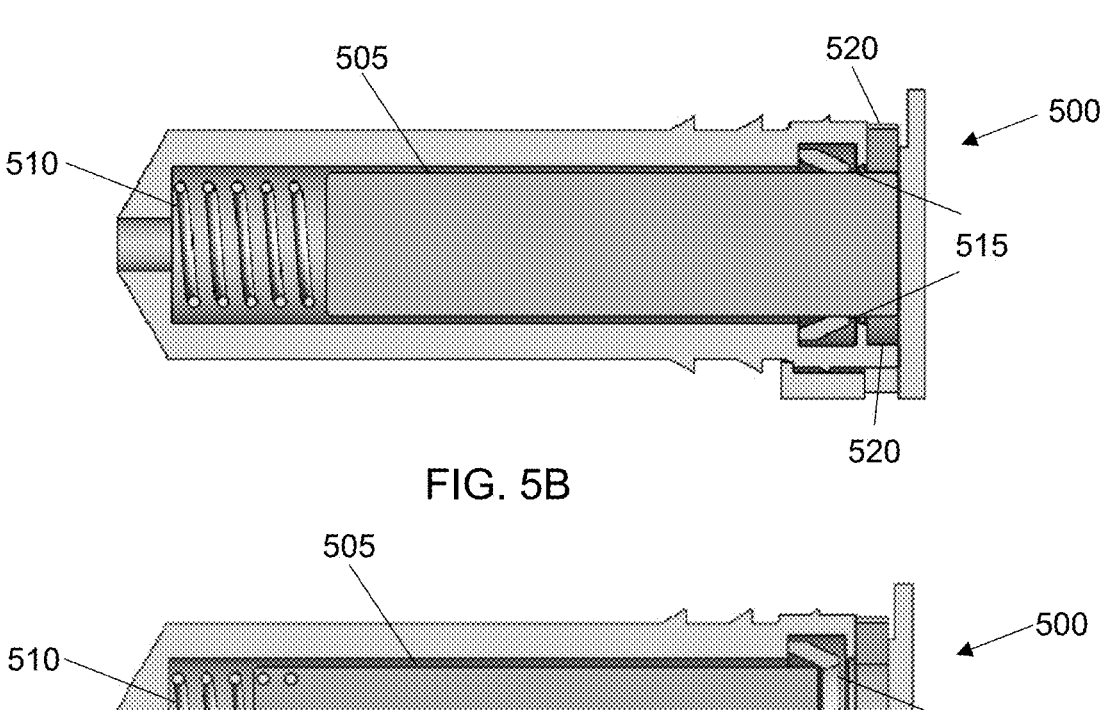
FIG. 5B
FIG. 5C
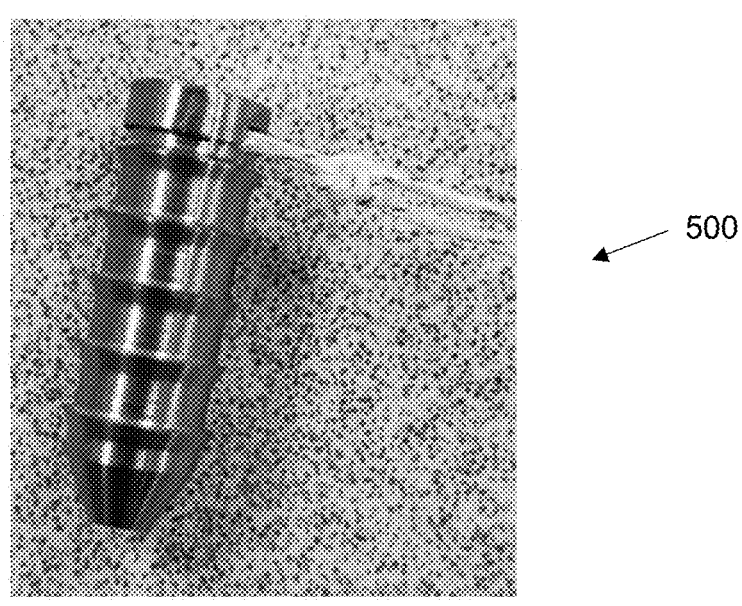
FIG. 5D

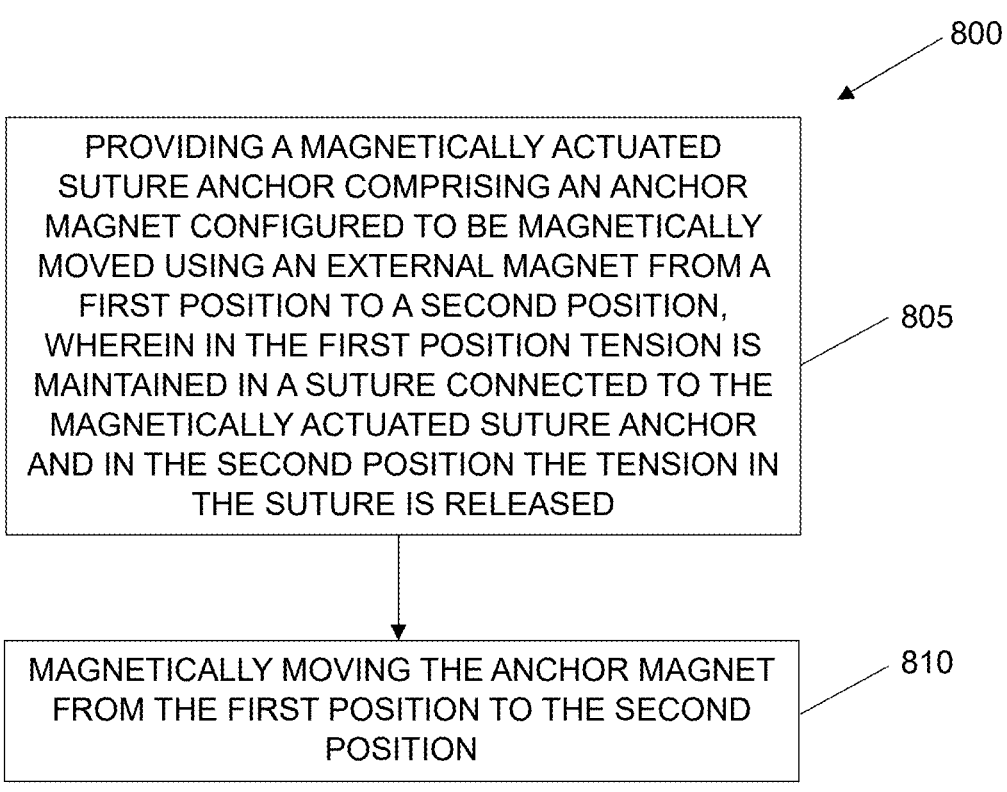

800

PROVIDING A MAGNETICALLY ACTUATED
SUTURE ANCHOR COMPRISING AN ANCHOR
MAGNET CONFIGURED TO BE MAGNETICALLY
MOVED USING AN EXTERNAL MAGNET FROM A
FIRST POSITION TO A SECOND POSITION,
WHEREIN IN THE FIRST POSITION TENSION IS
MAINTAINED IN A SUTURE CONNECTED TO THE
MAGNETICALLY ACTUATED SUTURE ANCHOR
AND IN THE SECOND POSITION THE TENSION IN
THE SUTURE IS RELEASED

805

MAGNETICALLY MOVING THE ANCHOR MAGNET
FROM THE FIRST POSITION TO THE SECOND
POSITION

EXTERNALLY MAGNETICALLY OPERATED SUTURE ANCHOR

CROSS-REFERENCE TO RELATED APPLICATIONS

This application claims priority to U.S. Provisional Application Ser. No. 63/632,886, filed Apr. 11, 2024, the entire contents of which are incorporated herein by reference.

TECHNICAL FIELD OF THE INVENTION

The present invention relates in general to a suture anchor, and more particularly, to a suture anchor that is releasable transcutaneously by magnetic operation.

STATEMENT OF FEDERALLY FUNDED RESEARCH

None.

BACKGROUND OF THE INVENTION

Without limiting the scope of the invention, the background of the invention is described in connection with a transcutaneously releasable suture anchor for extremity growth modulation without limiting the scope of the invention.

Extremity growth modulation for length and angular correction is common practice in adolescent orthopedics as a means of correcting limb length discrepancies and varus and valgus deformations, primarily in the lower limbs. Current practice is the placement of an "8-plate" that spans the epiphysis (growth plate), attaches to the adjacent metaphyses, and is secured to each metaphysis segment using screws. The metal plate limits bone growth locally by going into tension as the growth plate grows. In the case of angular deformation, this is done on one side of the growth plate, which allows the other side to "catch up." This uses the body's normal growth patterns to correct the deformity. While this is a proven and effective method of treating these types of abnormalities, a second surgery is required to remove the hardware and allow the growth plate to return to normal growth.

Methods and apparatuses that permit a release of tension in a device implanted to modulate growth in an extremity without the need for a second surgery is desirable.

SUMMARY OF THE INVENTION

As embodied and broadly described herein, an aspect of the present disclosure relates to a magnetically actuated suture anchor comprising: an anchor magnet configured to be magnetically moved using an external magnet from a first position to a second position, wherein in a first position a tension is maintained in a suture connected to the magnetically actuated suture anchor and in a second position the tension in the suture is released. In one aspect, the magnet is magnetically pushed using the external magnet. In another aspect, the magnetically actuated suture anchor further comprises an elastic energy storage unit configured and disposed to hold the anchor magnet in the first position; and a plurality of retaining fingers configured and disposed to hold the anchor magnet in the first position when the magnetically actuated suture anchor is in a tensioned state and in the second position when the magnetically actuated suture anchor is in a released state. In another aspect, the anchor magnet is magnetically pulled using the external magnet. In another aspect, the magnetically actuated suture anchor further comprises a suture winder; and a plunger connecting the anchor magnet to the suture winder, wherein the plunger is configured and disposed to be slidably inserted into and engaged with the suture winder when the anchor magnet is in the first position and the magnetically actuated suture anchor is in a tensioned state and configured and disposed to be slidably removed from the suture winder when the anchor magnet is moved the second position and the magnetically actuated suture anchor is in a released state. In another aspect, the magnetically actuated suture anchor further comprises a tension cleat; the anchor magnet connected to the tension cleat and configured and disposed to maintain tension in a suture; and an elastic energy storage unit connected to the tension cleat; wherein the anchor magnet is configured and disposed to be moved from the first position to the second position to release the tension cleat; wherein the elastic energy storage unit is configured and disposed to hold the tension cleat in place, wherein the anchor magnet is in the first position and the magnetically actuated suture anchor is in a tensioned state; and wherein the anchor magnet is configured and disposed to be moved to the second position and the magnetically actuated suture anchor is in a released state. In another aspect, the magnetically actuated suture anchor further comprises a plurality of retaining fingers configured and disposed to hold the anchor magnet in the first position when the anchor magnet is in the first position and the magnetically actuated suture anchor is in a tensioned state, and configured and disposed to hold the anchor magnet in the second position when the anchor magnet is in the second position the magnetically actuated suture anchor is in a released state. In another aspect, the anchor magnet comprises neodymium.

As embodied and broadly described herein, an aspect of the present disclosure relates to a magnetically actuated suture anchor kit comprising: a magnetically actuated suture anchor comprising an anchor magnet configured to be magnetically moved using an external magnet from a first position to a second position, wherein in a first position a tension is maintained in a suture connected to the magnetically actuated suture anchor and in a second position the tension in the suture is released; and one or more tools to manipulate the magnetically actuated suture anchor. In another aspect, the anchor magnet is magnetically pushed using the external magnet. In another aspect, the magnetically actuated suture anchor kit further comprises an elastic energy storage unit configured and disposed to hold the anchor magnet in the first position; and a plurality of retaining fingers configured and disposed to hold the anchor magnet in the first position when the magnetically actuated suture anchor is in a tensioned state and in the second position when the magnetically actuated suture anchor is in a released state. In another aspect, the anchor magnet is magnetically pulled using the external magnet. In another aspect, the magnetically actuated suture anchor further comprises a suture winder; and a plunger connecting the anchor magnet to the suture winder, wherein the plunger is configured and disposed to be slidably inserted into and engaged with the suture winder when the anchor magnet is in the first position and the magnetically actuated suture anchor is in a tensioned state and configured and disposed to be slidably removed from the suture winder when the anchor magnet is moved the second position and the magnetically actuated suture anchor is in a released state. In another aspect, the magnetically actuated suture anchor further comprises a tension cleat; the anchor magnet connected to the tension cleat and configured and disposed to maintain tension in a suture; and an elastic energy storage unit connected to the tension cleat; wherein the anchor magnet is configured and disposed to be moved from the first position to the second position to release the tension cleat; wherein the elastic energy storage unit is configured and disposed to hold the tension cleat in place wherein the anchor magnet is in the first position and the magnetically actuated suture anchor is in a tensioned state; and wherein the anchor magnet is configured and disposed to be moved to the second position and the magnetically actuated suture anchor is in a released state. In another aspect, the magnetically actuated suture anchor further comprises a plurality of retaining fingers configured and disposed to hold the anchor magnet in the first position when the magnet is in the first position and the magnetically actuated suture anchor is in a tensioned state, and configured and disposed to hold the anchor magnet in the second position when the magnet is in the second position the magnetically actuated suture anchor is in a released state. In another aspect, the anchor magnet comprises neodymium.

As embodied and broadly described herein, an aspect of the present disclosure relates to a method of releasing tension in a magnetically actuated suture anchor, the method comprising: providing a magnetically actuated suture anchor comprising an anchor magnet configured to be magnetically moved using an external magnet from a first position to a second position, wherein in the first position, a tension is maintained in a suture connected to the magnetically actuated suture anchor and in the second position the tension in the suture is released; and magnetically moving the anchor magnet from the first position to the second position. In one aspect, the anchor magnet is magnetically pushed using the external magnet. In another aspect, the magnetically actuated suture anchor further comprises an elastic energy storage unit configured and disposed to hold the anchor magnet in the first position; and a plurality of retaining fingers configured and disposed to hold the anchor magnet in the first position when the magnetically actuated suture anchor is in a tensioned state and in the second position when the magnetically actuated suture anchor is in a released state. In another aspect, the anchor magnet is magnetically pulled using the external magnet. In another aspect, the magnetically actuated suture anchor further comprises a suture winder; and a plunger connecting the anchor magnet to the suture winder, wherein the plunger is configured and disposed to be slidably inserted into and engaged with the suture winder when the anchor magnet is in the first position and the magnetically actuated suture anchor is in a tensioned state and configured and disposed to be slidably removed from the suture winder when the anchor magnet is moved the second position and the magnetically actuated suture anchor is in a released state. In another aspect, the magnetically actuated suture anchor further comprises a tension cleat; the anchor magnet connected to the tension cleat and configured and disposed to maintain tension in the suture; and an elastic energy storage unit connected to the tension cleat; wherein the anchor magnet is configured and disposed to be moved from the first position to the second position to release the tension cleat; wherein the elastic energy storage unit is configured and disposed to hold the tension cleat in place such that the anchor magnet is in the first position and the magnetically actuated suture anchor is in a tensioned state; and wherein the anchor magnet is configured and disposed to be moved to the second position and the magnetically actuated suture anchor is in a released state. In another aspect, the magnetically actuated suture anchor further comprises a plurality of retaining fingers configured and disposed to hold the anchor magnet in the first position when the anchor magnet is in the first position and the magnetically actuated suture anchor is in a tensioned state, and configured and disposed to hold the anchor magnet in the second position when the anchor magnet is in the second position and the magnetically actuated suture anchor is in a released state.

As embodied and broadly described herein, an aspect of the present disclosure relates to a method of treating a patient with a magnetically actuated suture anchor, the method comprising: providing a magnetically actuated suture anchor to the patient in need of extremity growth modulation, wherein the magnetically actuated suture anchor and a suture are used to control a growth or regrowth of bone in one or more directions; wherein the magnetically actuated suture anchor comprises an anchor magnet configured to be magnetically moved using an external magnet from a first position to a second position, wherein in the first position, a tension is maintained in a suture connected to the magnetically actuated suture anchor and in the second position the tension in the suture is released; and magnetically moving the anchor magnet from the first position to the second position. In another aspect, the magnetically actuated suture anchor is used as an internal brace to protect a surgically repaired ligament or tendon in a foot, ankle, knee, hip finger, thumb, wrist, elbow, shoulder, and medial or lateral clavicle, and released transcutaneously once sufficient healing has occurred. In another aspect, the magnetically actuated suture anchor is used as a releasable spinal tether in scoliosis treatment and released when an appropriate correction is attained. In another aspect, the magnetically actuated suture anchor is used to provide guided growth around physes in a shoulder, elbow, and wrist; guided growth around hip and pelvis; guided growth around a knee for a coronal or sagittal plane; guided growth around an ankle; dental alignment; as an internal brace to stabilize a foot, toe, or ankle bone alignment until healing has occurred; or to provide an internal brace to stabilize ankle sydesmosis until healing has occurred.

BRIEF DESCRIPTION OF THE DRAWINGS

For a more complete understanding of the features and advantages of the present invention, reference is now made to the detailed description of the invention along with the accompanying figures and in which:

FIGS. 4A-4D show various features of yet another embodiment of the present invention.

FIGS. 5A-5E show various features of still another embodiment of the present invention.

FIG. 8 shows a flowchart of a method embodiment of the present invention.

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

Disclosed herein are methods and apparatuses that include suture anchors and magnetic forces to release tension in the suture anchors. Suture anchors are commonly used to attach soft tissues, such as tendons and ligaments, to bone. Suture anchors in some circumstances are left in vivo permanently because there is rarely a need to remove them since they are usually embedded within the bone once healing has been completed. High-strength sutures, such as ultra-high molecular weight polyethylene (UHMWPE), exhibits exceptional properties in these types of applications. Embodiments of the invention disclosed herein include the use of a suture anchor to temporarily arrest growth by attaching it above and below the growth plate, with the suture placed in tension to counter growth locally. By using a suture anchor, the hardware may be left in the patient permanently. Embodiments of the invention also include the use of magnetic forces to release the suture without the need for an incision. In one example, a small magnet is used as a pin. Once the growth modulation treatment is completed, a magnet is brought up to the skin of the patient to manipulate the magnet of the suture anchor to release the suture. In this way, the treatment is concluded without incisions or additional surgery while also being completely pain-free.

Figures 1A, 1B, 1C:
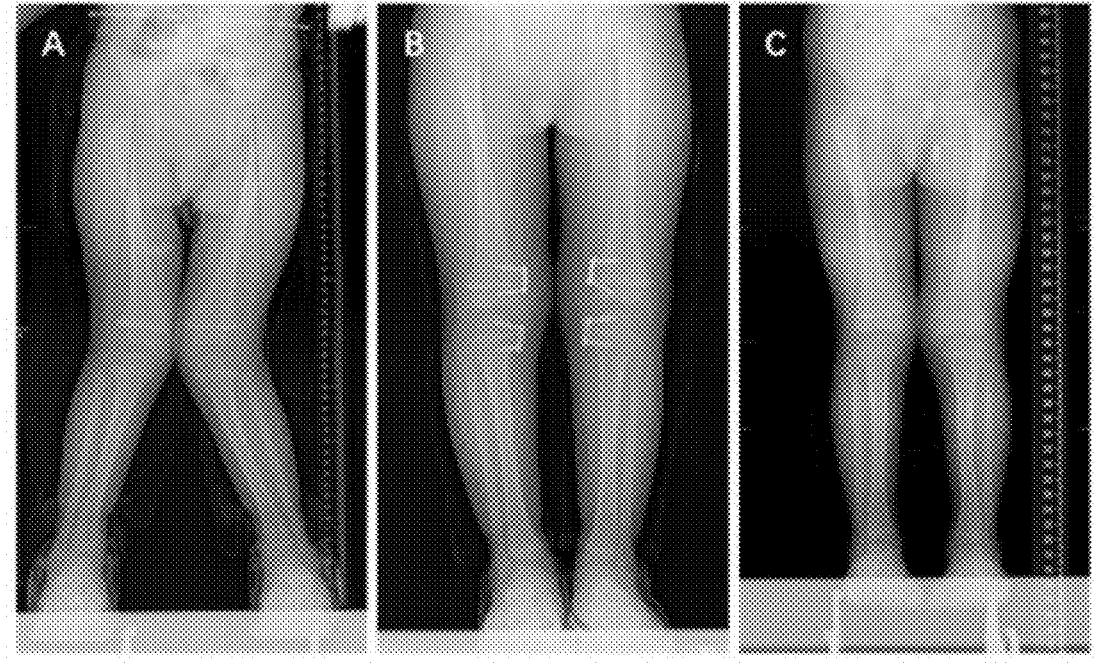
FIGS. 1A, 1B, and 1C show an image of the legs of a patient exhibiting valgus deformations, before, during, and after prior art treatment with 8-plates, respectively.

FIGS. 1A-1C show images of the prior-art use of 8-plates to treat valgus deformation of the knee. FIG. 1A shows untreated valgus deformation. FIG. 1B shows 8-plates placed in a first surgery on the medial distal femur and proximal tibia to temporarily halt medial growth. FIG. 1C shows the achieved correction with the 8-plates, which must be removed with a second surgery.

Embodiments of the invention disclosed herein includes the use of high-strength sutures, e.g., UHMWPE, which exhibits exceptional properties for attaching soft tissues (e.g., ligaments and tendons) to bone. The properties exhibited include very high strength, cut and abrasion resistance, very low friction, and minimal stretch. UHMWPE is used in some embodiments of the invention to restrain long-term growth across the physis. Embodiments also use magnetic actuation to release tension in the suture when treatment is complete. A magnet external to the body of the patient is used to push or pull a magnet or magnet-attracting material such as iron, nickel, or cobalt. Such magnetic actuation has several advantages. First, simple permanent magnets such as neodymium magnets can exert significant forces, and because the actuating magnet is outside the patient's body, there is no significant limiting principle on size and force. Further, a simple push or pull mechanism allows smaller, more compact sizing.

The suture anchor described herein can be used in a variety of ways, including but not limited to use as an internal brace to protect a surgically repaired ligament or tendon in a foot, ankle, knee, hip finger, thumb, wrist, elbow, shoulder, and medial or lateral clavicle, which can be released transcutaneously once sufficient healing has occurred.

In addition, the suture anchor described herein can be used as a releasable spinal tether in scoliosis treatment, which can be released upon an appropriate correction being attained. Further, the suture anchor described herein can be used in other ways, including but not limited to provide guided growth around physes in a shoulder, elbow, and wrist; guided growth around hip and pelvis; guided growth around a knee for a coronal or sagittal plane; guided growth around an ankle; dental alignment; to provide an internal brace to stabilize a foot, toe, or ankle bone alignment until healing has occurred; and to provide an internal brace to stabilize ankle sydesmosis until healing has occurred.

Figure 2A:
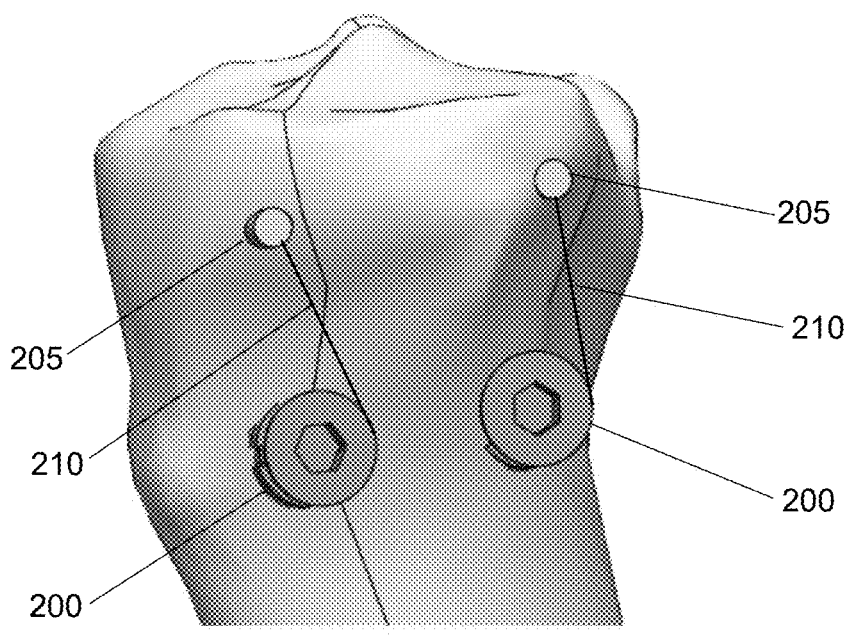
FIGS. 2A-2D show various views of an embodiment of the present invention.
Figure 2B:
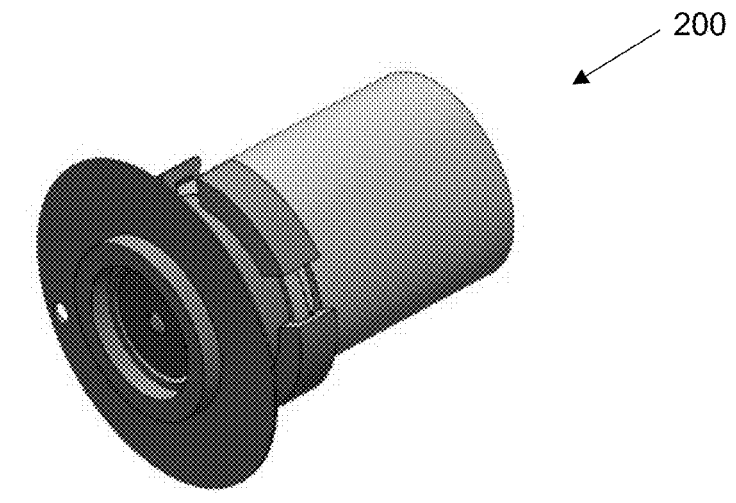
Figure 2C:
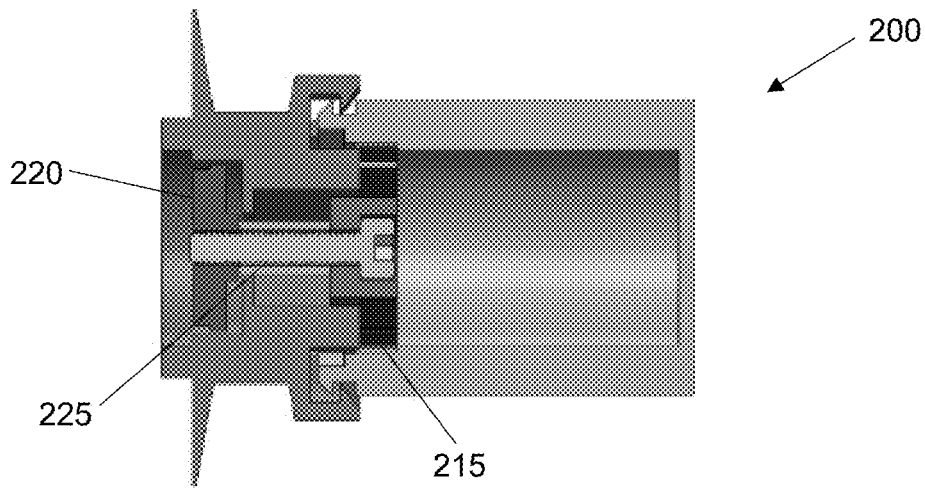
Figure 2D:
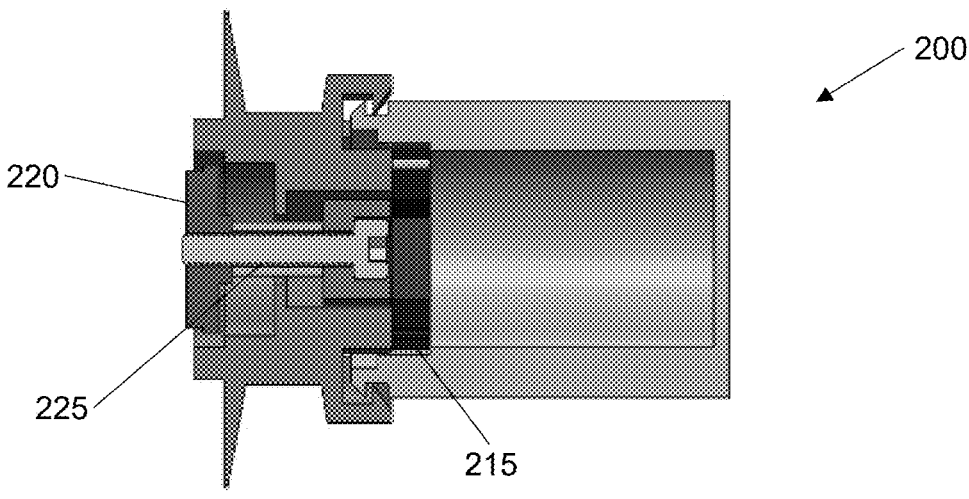

FIGS. 2A-2D show various views of an embodiment of the present invention. Two magnetically actuated suture anchors 200 are shown in FIG. 2A embedded in a bone, together with two static suture anchors 205 embedded in the bone. Each magnetically actuated suture anchor 200 is connected to a respective static suture anchor 205 with a suture 210. FIG. 2B shows an exterior view of the magnetically actuated suture anchor 200. FIG. 2C shows a cross-section of the magnetically actuated suture anchor 200 in a state in which the suture 210 is tensioned, including a suture winder 215 that is used to tension the suture 210 (not shown in FIG. 2C) and an anchor magnet 220 that is connected to the suture winder 215 with a plunger 225 that is slidably insertable and removable from the suture winder 215. FIG. 2D shows a cross-section of the magnetically actuated suture anchor 200 in a state in which the suture 210 (not shown in FIG. 2D) is released so that it is not tensioned, including the suture winder 215, the anchor magnet 220, and the plunger 225. In FIG. 2D, the anchor magnet 220 has been magnetically pulled out from the position shown in FIG. 2C using an external magnet (not shown), slidably removing the plunger 225 from the suture winder 215 and releasing tension in the suture 210 without the need for surgery.

Figure 3A:
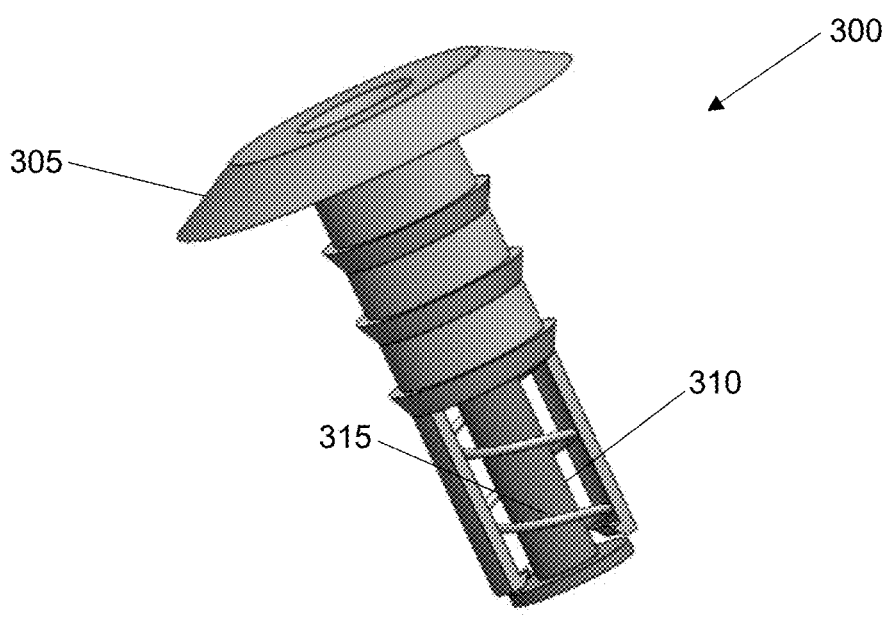
FIGS. 3A-3D show various features of another embodiment of the present invention.
Figure 3B:
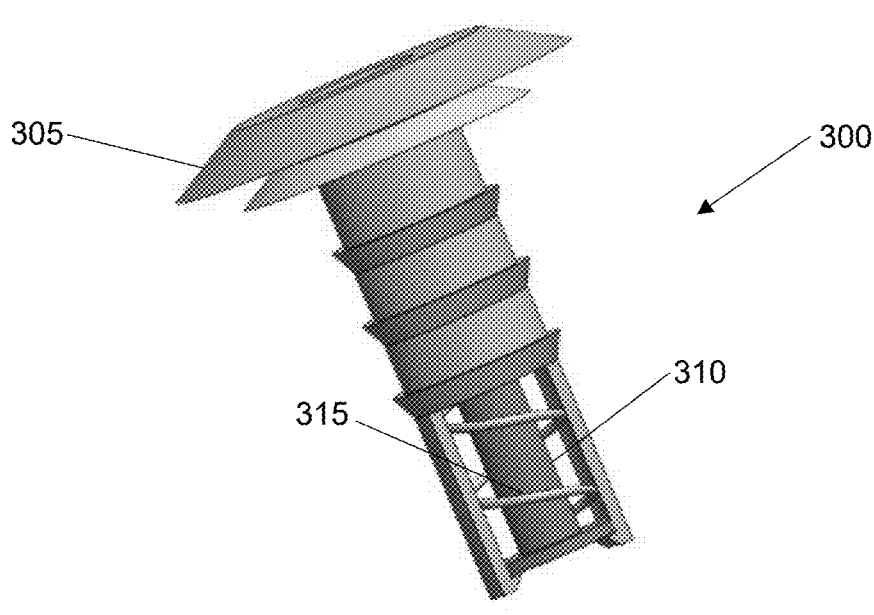

FIGS. 3A and 3B show various features of another embodiment of the present invention. FIG. 3A shows a view of a magnetically actuated suture anchor 300 in a tensioned state, including a tension cleat 305 holding a tensioned suture (not shown in FIG. 3A) and connected to an anchor magnet 310 and an elastic energy storage unit 315 (e.g., a spring). In the tensioned state, the tension cleat 305 holds the suture in tension while the elastic energy storage unit 315 exerts a force to hold the tension cleat 305 in place. FIG. 3B shows a view of the magnetically actuated suture anchor 300 in a released state. In FIG. 3B, the anchor magnet 310 has been pulled against the force exerted by the elastic energy storage unit 315 to release the tension cleat 305, thus releasing the tension in the suture (not shown in FIG. 3B).

Figure 3C:
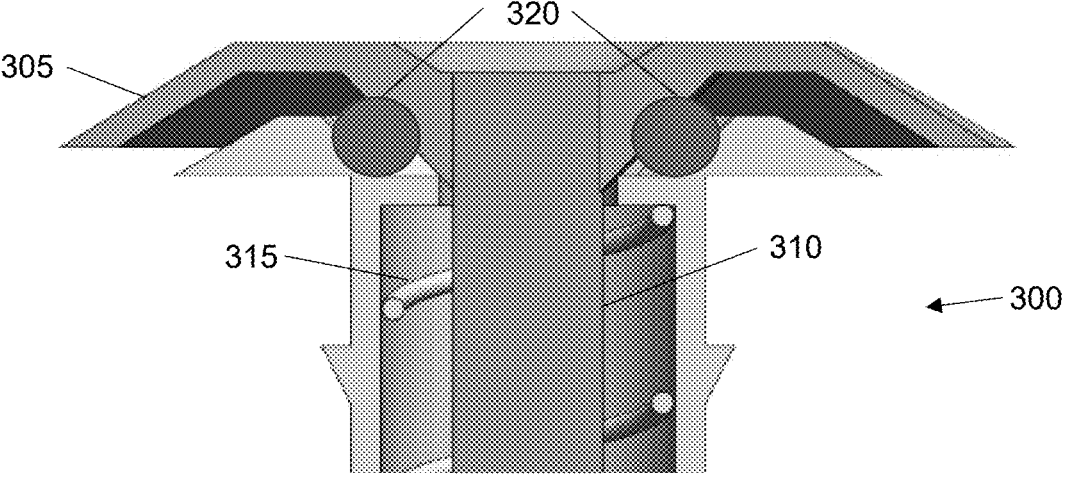

FIG. 3C shows a cross-section of the magnetically actuated suture anchor 300 in the tensioned state (see FIG. 3A), including the tension cleat 305, the anchor magnet 310, elastic energy storage unit 315, and the suture 320.

Figure 3D:
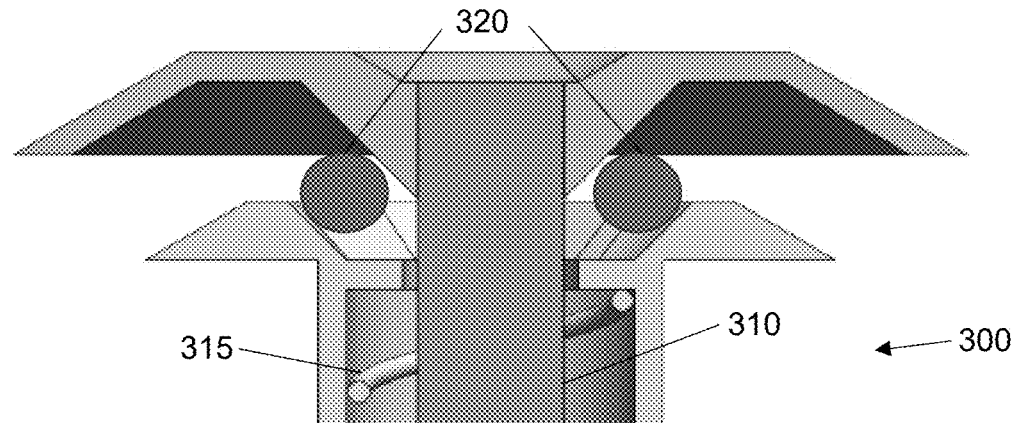

FIG. 3D shows a cross section of the magnetically actuated suture anchor 300 in the released state (see FIG. 3B), including the tension cleat 305, the anchor magnet 310, elastic energy storage unit 315, and the suture 320. In FIG. 3D, the anchor magnet 310 has been magnetically pulled out from the position shown in FIG. 3C using an external magnet (not shown), releasing the tension cleat 305 and releasing tension in the suture without the need for surgery.

Figure 4D:
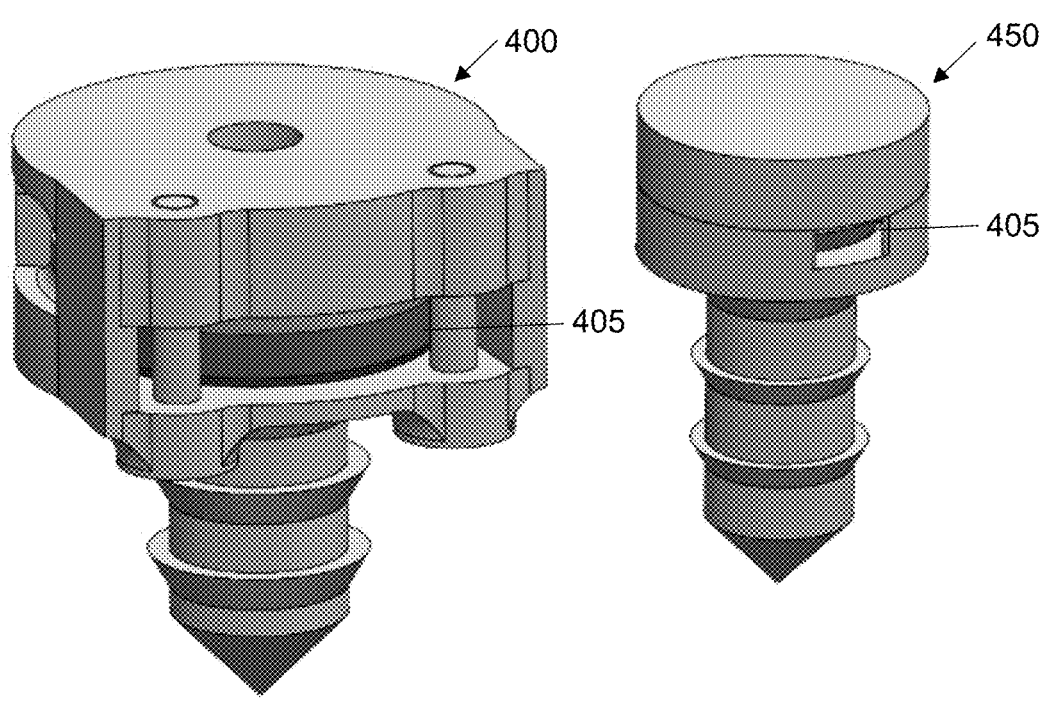

FIGS. 4A-4D show various features of yet another embodiment of the present invention. FIG. 4A shows a cutaway view of a magnetically actuated suture anchor 400 in a tensioned state by an anchor magnet 405. FIG. 4B shows a cross-sectional view of the magnetically actuated suture anchor 400 in the tensioned state (see FIG. 4A) with the anchor magnet 405, one of a plurality of retaining fingers 410, and a suture 415. In the tensioned state, the plurality of retaining fingers 410 retain the anchor magnet 405 in the position shown, which is required to maintain tension in the suture 415. FIG. 4C shows a cross-sectional view of the magnetically actuated suture anchor 400 in a released state, with the anchor magnet 405, one of a plurality of retaining fingers 410, and a suture 415. In the released state, the plurality of retaining fingers 410 retain the anchor magnet 405 in the position shown, and tension in the suture 415 is released. In FIG. 4C, the anchor magnet 405 has been magnetically pulled out from the position shown in FIG. 4B using an external magnet (not shown), releasing tension in the suture 415 without the need for surgery. FIG. 4D shows magnetically actuated suture anchor 400 alongside a smaller embodiment, a magnetically actuated suture anchor 450, in which the anchor magnet 405 is magnetically pushed downward and the motion to release tension in the suture 415 (not shown) is positioned in the bone portion of the magnetically actuated suture anchor 450, reducing the profile of the magnetically actuated suture anchor 450 above the bone.

Figure 5A:
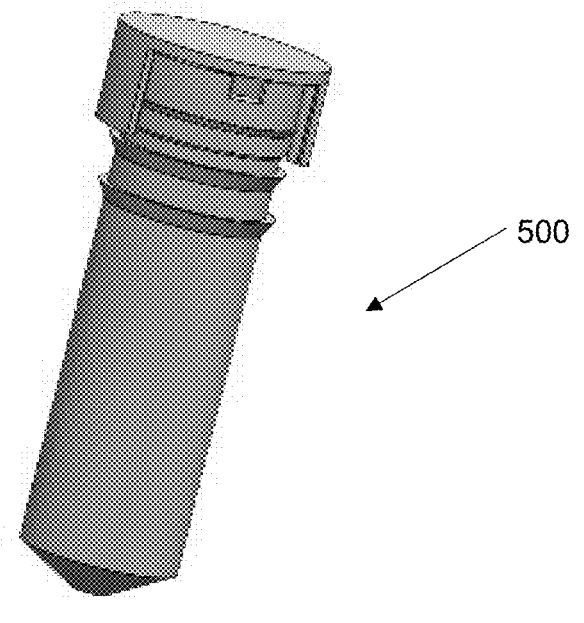
Figure 5E:
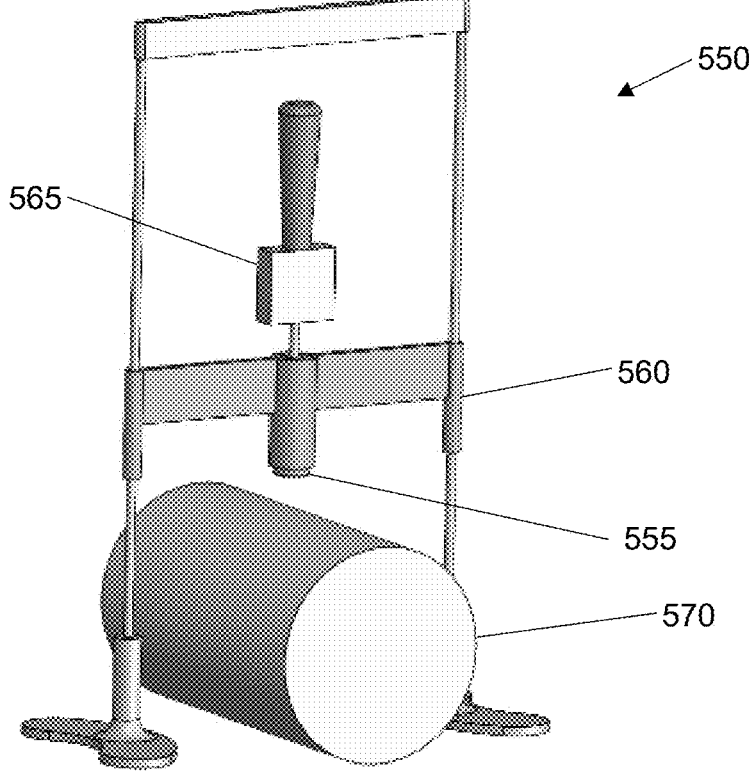

FIGS. 5A-5E show various features of still another embodiment of the present invention. FIG. 5A shows an exterior view of a magnetically actuated suture anchor 500. FIG. 5B shows the magnetically actuated suture anchor 500 in a tensioned state, with anchor magnet 505, elastic energy storage unit 510 (e.g., a spring), two of a plurality of retaining fingers 515, and a suture 520. In the tensioned state, the elastic energy storage unit 510 holds the anchor magnet 505 in place in the position shown, which is required to maintain tension in the suture 520. FIG. 5C shows the magnetically actuated suture anchor 500 in a released state, the plurality of retaining fingers 515 holding the anchor magnet 505 in the position shown, the elastic energy storage unit 510 is compressed relative to status in the tensioned state, and tension in the suture 520 is released. In FIG. 5C, the anchor magnet 505 has been magnetically pushed from the position shown in FIG. 5B using an external magnet (not shown), releasing tension in the suture 520 without the need for surgery. FIG. 5D shows an image of the magnetically actuated suture anchor 500. FIG. 5E shows an exemplary deployment tool 550 to use to move the anchor magnet 505 (not shown in FIG. 5E) to release tension in the suture 520 (not shown in FIG. 5E). The deployment tool 550 includes a deployment magnet 555 mounted on a slider 560 and optionally a force gauge 565. The deployment tool 550 is used to align the deployment magnet 555 with the anchor magnet 505 and move the deployment magnet 555 on the slider 560 toward the anchor magnet 505 to push the anchor magnet 505 from the tensioned position shown in FIG. 5B to the released position shown in FIG. 5C. The force gauge 565 is used to help determine when the force required to push the anchor magnet 505 from the tensioned position to the released position has been reached. The deployment tool is shown set up over a patient's leg 570.

The anchor magnets 220, 310, 405, and 505, and any magnets included in other embodiments of the present invention may comprise, e.g., neodymium.

Figure 6A:
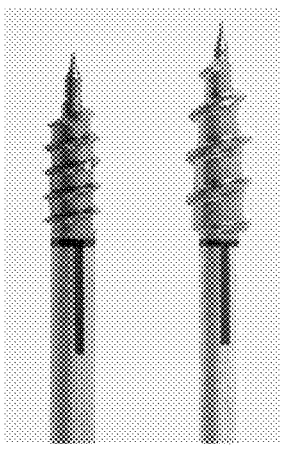
FIGS. 6A-6C show exemplary alternative static suture anchors to be used with embodiments of the present invention.
Figure 6B:
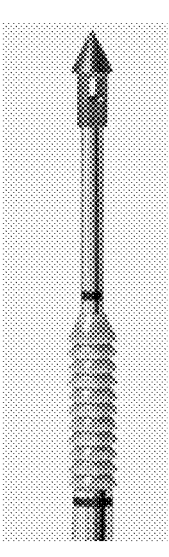
Figure 6C:
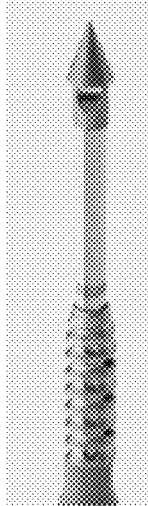

FIGS. 6A-6C show exemplary alternative static suture anchors to be used with embodiments of the present invention, e.g., the static suture anchors 205 shown in FIG. 2A. FIG. 6A shows a corkscrew FT 600 (fully threaded), comprising titanium and featuring a knot suture tension hold. FIG. 6B shows a PushLock® SP (self-punching), comprising a titanium tip and a PEEK bone anchor. FIG. 6C shows a SwiveLock® SP (self-punching), comprising titanium and using UHMWPE swaged between the tip and the interior of the screw.

Figures 7A, 7B:
FIG. 7A shows a patient with a valgus deformity of both knees.
FIG. 7B shows the patient after completion of treatment using growth modulation techniques.

FIG. 7A shows a typical valgus deformity that was treated using temporary growth arrest on the middle side of the knee to permit the lateral side of the growth plate to grow unconstrained and thereby straighten the leg, as shown in FIG. 7B.

FIG. 8 shows a flowchart of a method embodiment of the present invention. Method 800 includes block 805, providing a magnetically actuated suture anchor comprising an anchor magnet configured to be magnetically moved using an external magnet from a first position to a second position, wherein in the first position tension is maintained in a suture connected to the magnetically actuated suture anchor and in the second position the tension in the suture is released. Method 800 also includes block 810, magnetically moving the anchor magnet from the first position to the second position.

An embodiment of the present invention includes a magnetically actuated suture anchor kit including a magnetically actuated suture anchor comprising an anchor magnet configured to be magnetically moved using an external magnet from a first position to a second position, wherein in a first position a tension is maintained in a suture connected to the magnetically actuated suture anchor, and in a second position the tension in the suture is released; This kit includes, e.g., one or more of the magnetically actuated suture anchors 200, 300, 400, and 500.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), propertie(s), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

Additionally, the section headings herein are provided for consistency with the suggestions under 37 CFR 1.77 or otherwise to provide organizational cues. These headings shall not limit or characterize the invention(s) set out in any claims that may issue from this disclosure. Specifically and by way of example, although the headings refer to a "Field of Invention," such claims should not be limited by the language under this heading to describe the so-called technical field. Further, a description of technology in the "Background of the Invention" section is not to be construed as an admission that technology is prior art to any invention(s) in this disclosure. Neither is the "Summary" to be considered a characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of such claims shall be considered on their own merits in light of this disclosure, but should not be constrained by the headings set forth herein.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

To aid the Patent Office, and any readers of any patent issued on this application in interpreting the claims appended hereto, applicants wish to note that they do not intend any of the appended claims to invoke paragraph 6 of 35 U.S.C. § 112, U.S.C. § 112 paragraph (f), or equivalent, as it exists on the date of filing hereof unless the words "means for" or "step for" are explicitly used in the particular claim.

For each of the claims, each dependent claim can depend both from the independent claim and from each of the prior dependent claims for each and every claim so long as the prior claim provides a proper antecedent basis for a claim term or element.

What is claimed is:

1. A magnetically actuated suture anchor comprising:
an anchor magnet configured to be magnetically moved using an external magnet from a first position to a second position, wherein the anchor magnet is magnetically pulled using the external magnet, and wherein in the first position a tension is maintained in a suture connected to the magnetically actuated suture anchor and in the second position the tension in the suture is released;
a suture winder; and
a plunger connecting the anchor magnet to the suture winder, wherein the plunger is configured and disposed to be slidably inserted into and engaged with the suture winder when the anchor magnet is in the first position and the magnetically actuated suture anchor is in a tensioned state and configured and disposed to be slidably removed from the suture winder when the anchor magnet is moved to the second position and the magnetically actuated suture anchor is in a released state.

2. The magnetically actuated suture anchor of claim 1, wherein the anchor magnet is magnetically pushed using the external magnet.

3. The magnetically actuated suture anchor of claim 1, wherein the anchor magnet comprises neodymium.

4. A magnetically actuated suture anchor kit comprising:
a magnetically actuated suture anchor comprising:
an anchor magnet configured to be magnetically moved using an external magnet from a first position to a second position, wherein the anchor magnet is magnetically pulled using the external magnet, and wherein in the first position a tension is maintained in a suture connected to the magnetically actuated suture anchor and in the second position the tension in the suture is released;

a suture winder; and a plunger connecting the anchor magnet to the suture winder, wherein the plunger is configured and disposed to be slidably inserted into and engaged with the suture winder when the anchor magnet is in the first position and the magnetically actuated suture anchor is in a tensioned state and configured and disposed to be slidably removed from the suture winder when the anchor magnet is moved the second position and the magnetically actuated suture anchor is in a released state; and one or more tools to manipulate the magnetically actuated suture anchor.

5. The magnetically actuated suture anchor kit of claim 4, wherein the anchor magnet is magnetically pushed using the external magnet.

6. The magnetically actuated suture anchor kit of claim 4, wherein the anchor magnet comprises neodymium.

7. A method of releasing tension in a magnetically actuated suture anchor, the method comprising:

providing a magnetically actuated suture anchor comprising:

an anchor magnet configured to be magnetically moved using an external magnet from a first position to a second position, wherein in the first position, a tension is maintained in a suture connected to the magnetically actuated suture anchor and in the second position the tension in the suture is released;

a suture winder; and a plunger connecting the anchor magnet to the suture winder; and magnetically moving the anchor magnet from the first position to the second position, wherein the anchor magnet is magnetically pulled using the external magnet;

wherein the plunger is configured and disposed to be slidably inserted into and engaged with the suture winder when the anchor magnet is in the first position and the magnetically actuated suture anchor is in a tensioned state and configured and disposed to be slidably removed from the suture winder when the anchor magnet is moved to the second position and the magnetically actuated suture anchor is in a released state.

8. The method of claim 7, wherein the anchor magnet is magnetically pushed using the external magnet.

* * * * *